United States Patent [19]

Yudovich

[11] 4,375,570
[45] Mar. 1, 1983

[54] METHOD OF TREATING ALPHA-METHYLBENZYL ALCOHOL DEHYDRATION RESIDUES

[75] Inventor: Amos Yudovich, Tulsa, Okla.

[73] Assignee: Atlantic Richfield Company, Los Angeles, Calif.

[21] Appl. No.: 375,238

[22] Filed: May 5, 1982

[51] Int. Cl.³ .................. C07C 12/64; C07C 1/253
[52] U.S. Cl. .................... 585/410; 585/241; 585/435; 585/476
[58] Field of Search ........... 585/410, 413, 476, 435, 585/437, 241; 208/125, 126, 128

[56] References Cited

U.S. PATENT DOCUMENTS

| | | | |
|---|---|---|---|
| 2,248,512 | 7/1941 | Philip et al. | 585/439 |
| 2,359,212 | 9/1944 | Frank et al. | 585/241 |
| 2,395,829 | 3/1946 | King | 585/241 |
| 2,929,855 | 3/1960 | O'Connor et al. | 585/241 |
| 3,396,206 | 8/1968 | Scott | 585/435 |
| 3,658,928 | 4/1972 | Skinner | 585/437 |
| 4,273,622 | 6/1981 | Becker | 203/28 |

FOREIGN PATENT DOCUMENTS 771079  1/1979  U.S.S.R. .................. 585/435

Primary Examiner—Delbert E. Gantz
Assistant Examiner—A. Pal
Attorney, Agent, or Firm—Craig E. Larson

[57] ABSTRACT

Residual products obtained in the catalytic dehydration of alpha-methylbenzyl alcohol are treated to recover increased quantities of ethylbenzene by a process which comprises thermally cracking the residual products in the substantial absence of hydrogen under elevated pressures.

7 Claims, No Drawings

METHOD OF TREATING ALPHA-METHYLBENZYL ALCOHOL DEHYDRATION RESIDUES

BACKGROUND OF THE INVENTION

This invention relates to the dehydration of alpha-methylbenzyl alcohol (also known as alpha-phenylethanol or methyl phenyl carbinol) to produce styrene. The invention is more particularly concerned with the recovery of valuable monomeric compounds from residual materials produced in the separation of components of the dehydrated mixture.

An early process by which styrene was produced commercially for a short period of time comprised oxidation of ethylbenzene to acetophenone in the liquid phase, hydrogenation of the ketone to alpha-methylbenzyl alcohol, and catalytic dehydration of the alcohol through styrene. This process is described in Kirk-Othmer, "Encyclopedia of Chemical Technology," 1954, Volume 13, pp. 134–36. A more recent, commercial process for the dehydration of alpha-methylbenzyl alcohol is described on pp. 62–63 of the above-mentioned Volume 19 of the 2nd edition of the Kirk-Othmer text. The dehydration of ethylmethylbenzyl alcohol can be effected in any convenient manner, either in the liquid phase or in the vapor phase. See for example the methods described in U.S. Pat. No. 3,658,928. A particularly attractive process is the liquid phase dehydration process described in Becker et al. U.S. Pat. No. 3,526,674 issued Sept. 1, 1970, disclosure which patent is incorporated herein by reference.

According to the process described in the Becker patent, alpha-methylbenzyl alcohol is subjected to catalytic dehydration in the presence of a liquid-phase reaction medium at a temperature above about 200° C., but below the decomposition temperature of the liquid phase reaction medium, in the presence of an appropriate catalyst. Ordinarily, the liquid-phase medium is provided by accumulating a sufficient quantity of the residual material which is formed during the dehydration reaction. These residual materials are retained in the dehydration system, except for a relatively small purge to prevent an undesired buildup. The residual material can be the sole liquid-phase reaction medium or it can be mixed with either polar or non-polar, relatively high boiling solvents of the type described in the Becker patent. During the course of the reaction, the alpha-methylbenzyl alcohol forms water and the desired styrene. Under the reaction conditions employed in the Becker process, the water and styrene are volatilized substantially as rapidly as they are formed and are therefore readily removed from the reaction zone. Alpha-methylbenzyl alcohol can also be volatilized as the reaction proceeds and is suitably condensed and returned to the reaction zone. The small amounts of high-boiling residual by-products remain essentially unvolatilized and are purged from the liquid-phase medium, periodically or continuously, when they accumulate to an undesired extent.

The purged stream which is thus withdrawn from the liquid-phase reaction medium ordinarily represents a very minor quantity and its withdrawl does not effect the commercial attractiveness of the process. However, treatment of this purge stream is known to yield additional quantities of styrene and styrene precursors, increasing the overall styrene selectivity of the process and reducing waste disposal problems.

In the case of vapor-phase operation, a residual by-product fraction may also be recovered from the vaporous effluent from the reactor and what has been said above regarding the residual purge from liquid-phase dehydration is also applicable to such vapor-phase residual fractions.

U.S. Pat. No. 4,273,622 discloses a process wherein the residual portion of the alpha-methylbenzyl alcohol dehydrate is distilled in two stages, the first stage being carried out at a temperature of 180° C. to 275° C. under vacuum, and the second stage treatment of the first stage residue being carried out at a higher temperature than the first stage temperature for a longer period of time. Preferred second stage temperatures are within the range from 300° C. to 425° C. Although second stage pressure is not disclosed to be critical, preferred pressures are at least 500 mm Hg and are at about atmospheric pressure.

Recovery of styrene monomer from polystyrene by thermal cracking at temperatures excess of 300° C. is known. Common by-products from thermal cracking of polystyrene are toluene, ethylbenzene and alpha-methylstyrene.

Dehydration residues contain predominantly polymeric materials (largely polystyrenes) although minor amounts (about 2–10 wt. percent) of styrene monomer, acetophenone, alpha-methylbenzyl alcohol, beta-phenylethanol, and 1,4 dipropyl benzene may also be present. Polymeric materials include polymeric hydrocarbons, polymeric oxygenated materials and interpolymer or condensation products containing both hydrocarbon and oxygenated moieties.

When this residual material is treated directly at temperatures necessary to achieve the polymerization, the 4,273,622 patent notes the contained monomeric components react with polymeric components to form additional polymeric substances which result in a significantly more refractory polymeric mass. By employing the particular distillation regimen disclosed in the 4,273,622 patent, these undesired reactions can be avoided and polymeric components are converted into significant percentages of styrene monomer and other valuable monomers.

U.S. Pat. No. 2,929,855 is concerned with residues obtained as by-products in the preparation of styrene from ethylbenzene by oxidation of ethylbenzene to acetophenone, hydrogenation of acetophenone to alpha-methylbenzyl alcohol and dehydration of alpha-methylbenzyl alcohol to styrene. The treatment method disclosed comprises hydrogenolysis of the residues at 400° C. to 700° C. and pressures above 500 psi. Hydrogen is provided at the rate of 4–10 lbs. per 100 lbs. of feed. Hydrogen feed rates below 2 lbs. per 100 lbs. of residue feed are avoided because of coke formation in the reactor. Preferred hydrogenolysis operating conditions are 500°–600° C. and 2,000–4,000 psi. Products recovered from the process are benzene, toluene and ethylbenzene.

The 4,273,622 and 2,929,855 patents both teach useful methods for the recovery of valuable products from alphamethylbenzyl alcohol dehydration residues. However, neither method has been found entirely satisfactory for commercial application. The principal drawback for the 4,273,622 is the need for a difficult and expensive separation of styrene and ethylbenzene in the product. The principal drawbacks of the 2,929,855 method are the severe operating conditions employed and attended high capital equipment costs.

An object of this invention is to provide an improved process for recovering valuable products from the residual portion of the reaction mixture obtained in the dehydration of alpha-methylbenzyl alcohol. A further object of this invention is a method for the recovery of valuable products from alpha-methylbenzyl alcohol dehydration residue which method is compatable with, and enhances the yields of, liquid-phase dehydration processes of the type described in the Becker patent. Other objects will be apparent from the following description of this invention.

SUMMARY OF THE INVENTION

The process of this invention is a method for the recovery of aromatic hydrocarbons from dehydration residues obtained in the preparation of styrene from alpha-methylbenzyl alcohol. The method comprises thermally cracking the residues at elevated pressures within the range from about 75 to 300 psig, withdrawing the cracked effluent from the reaction zone and recovering liquid aromatic hydrocarbons from the cracked effluent. Thermal cracking at elevated pressures has surprisingly been found to substantially raise the ethylbenzene content and substantially lower the styrene monomer content of the recovered aromatic hydrocarbons. Thus, pressure has been found to be a process variable useful for controlling the styrene/ethylbenzene ratios in the thermally cracked effluent. This discovery has led to the development of an alpha-methylbenzyl alcohol dehydration residue treatment method which produces a $C_8$ hydrocarbon composed primarily of ethylbenzene and having low amounts (preferably less than 3 wt. percent) of styrene.

The method of this invention therefore avoids the costly ethylbenzene/styrene monomer separations occasioned by prior art methods such as that taught by U.S. Pat. No. 4,273,622, without necessitating the severe operating conditions of U.S. Pat. No. 2,929,855. The recovered liquid aromatics may advantageously be recycled to the dehydration process as will be described in the following detailed description.

A further discovery is that valuable aromatic hydrocarbos may be continuously produced from dehydration residues under thermal cracking conditions.

DETAILED DESCRIPTION OF THE INVENTION

The residue treated according to this invention may be the residual fraction remaining after the products of vapor-phase, alpha-methylbenzyl alcohol dehydration are distilled to recover a styrene fraction. However, this invention is particularly applicable to the residual by-product, withdrawn as a purge stream, from liquid-phase dehydration operations. The term "dehydration residues," as used herein, refers to any such residual fraction which may be produced in any alpha-methylbenzyl alcohol dehydration process. The term refers to the first polymer-containing residue obtained in the preparation of styrene by dehydration of alpha-methylbenzyl alcohol.

The residue is a multi-component material comprising predominantly polymeric materials but may also contain small amounts of alpha-methylbenzyl alcohol, acetophenone, ethylbenzene, styrene monomer, and, in the case of liquid-phase dehydration, catalyst. The quantity of monomeric components may range broadly from 1 to 20 wt. percent but usually will range from about 2 to 10 wt. percent. Liquid-phase dehydration residues contain small amounts (1–10 wt. percent) of catalyst, e.g. alumina, but the catalyst has been found to have no effect on the method of this invention.

The dehydration residues are thermally cracked at a temperature within the range of from about 325° C. to 475° C., preferably 350° C.–450° C., and more preferably from about 400° C.–425° C. Reactor wall temperatures should not exceed about 500° C. to prevent reactor fouling by coke formation.

The pressure in the thermal cracking step may range broadly about from 75 to 300 psig, although the pressure is preferably in the range from about 100–250 psig. As shown in the examples of the specification, the use of these elevated pressures dramatically effects the styrene/ethylbenzene ratio of the cracked product.

The design of the cracking reactor is not critical to the present invention. Either plug-flow or back-mixed systems may be employed. However, back-mixed systems, or stirred tank reactors, are preferred because of their simplicity.

Residence times within the thermal cracking reactor effect both the $C_8$ yield of the process and the composition of the $C_8$ product fraction. Broadly, the residence time may range from about 20 minutes to 3 hours. Preferably, the residence time is within the range from about 40 to 70 minutes.

Products from thermal cracking include a heavy fraction which may be burned as fuel and a light fraction comprising: $C_8$ aromatics, toluene, and $C_9$ aromatics. The $C_8$ aromatics are predominantly ethyl benzene containing minor amounts of acetophenone and styrene monomer. The $C_9$ aromatics are predominantly cumene containing minor amounts of alpha-methyl styrene.

At the reaction conditions employed, the normally liquid aromatic products are volatilized substantially as rapidly as they are formed. Therefore, they are readily separated from the heavy fraction of the thermally cracked effluent.

A typical composition of this overhead product is shown below in Table VI. Preferably, toluene is separated from the overhead product in separation means such as a distillation column. The remaining product, comprising ethylbenzene, may then be recycled for further processing. In a preferred embodiment, the method of this invention is applied to dehydration residues formed in a multi-step process for producing styrene for ethylbenzene. This known process comprises:

(a) oxidizing ethylbenzene to ethylbenzene hydroperoxide;

(b) containing the hydroperoxide with an olefin to form the corresponding olefin oxide and alpha-methylbenzyl alcohol;

(c) removing unreacted olefin and its epoxide from the mixture of compounds produced in step (b);

(d) recovering unreacted ethylbenzene from the olefin-and-epoxide free mixture produced in step (c) and recycling the recovered ethylbenzene to step (a);

(e) recovering alpha-methylbenzyl alcohol from the mixture remaining after ethylbenzene recovery step (d);

(f) subjecting the recovered alpha-methylbenzyl alcohol to liquid-phase catalytic dehydration to form a crude styrene overhead product and a dehydration residue.

It is contemplated that the light fraction produced by thermally cracking dehydration residue (preferably after removal of toluene) pass to ethylbenzene recovery step (d). Prior to passing the light fraction to the ethylbenzene recovery step, it may be subjected to catalytic hydrogenation to convert acetophenone to alpha-methylbenzyl alcohol, allowing production of additional quantities of styrene in dehydration step (f).

The following examples will further illustrate the process of this invention.

EXAMPLE 1

Dehydration residue from the manufacture of styrene was thermally cracked at varying pressures in a coiled, ¼ inch, 316 stainless steel tube continuous reactor. The reactor temperature was maintained at 450° C. The reactor volume divided by the volumetric flow rate (liquid feed at ambient conditions) was about 25 minutes. Cracked product from the reactor was flashed through an expansion valve into a vapor-liquid separator. Vapors were condensed in a water-cooled glass condenser and collected as overhead product. A portion of the liquid from the separator was collected as bottoms product and a portion was recycled to the reactor. The recycle ratio was 2.6:1 (recycle flow rate: feed flow rate). Composition of the overhead product (expressed as grams/100 grams dehydration residue reacted) as a function of pressure as shown in Table I below.

TABLE I

|  | Pressure (psig) | | | | |
| --- | --- | --- | --- | --- | --- |
|  | 10 | 50 | 100 | 200 | 300 |
| Total $C_8$'s | 37.4 | 33.4 | 41.6 | 42.2 | 30.8 |
| Ethylbenzene | 13.2 | 13.6 | 30.8 | 36.6 | 26.7 |
| Styrene | 21.0 | 16.4 | 5.7 | 0.8 | 1.3 |
| Acetophenone | 3.2 | 3.4 | 5.1 | 4.8 | 2.8 |
| Toluene | 12.9 | 12.6 | 18.0 | 28 | 17.6 |
| Total $C_9$'s | 8.2 | 6.8 | 7.2 | 7.0 | 7.0 |
| Cumene | 1.6 | 1.7 | 3.9 | 6.3 | 5.9 |
| α-methylstyrene | 6.4 | 5.1 | 3.3 | 0.7 | 1.1 |
| Styrene/Ethylbenzene | 1.6 | 1.2 | 0.19 | 0.02 | 0.05 |

An analysis of the gas present in the vapor-liquid separator and the condensor showed about 1.2 volume percent $H_2$ at both 10 and 200 psig reactor pressures.

On the one hand, increasing pressure dramatically lowers styrene monomer production (from 21 grams/100 residue feed at 10 psig to about 1 gram/100 grams residue feed at 200–300 psig). On the other hand, increasing pressure sharply raises ethyl benzene production (from 13 grams/100 grams of residue feed at 10 psig to 37 grams/100 grams residue at 200 psig). Total $C_8$ recovery is not a strong function of pressure within the range of pressures studied although repolymerization reactions may decrease $C_8$ recovery as pressures approach and exceed 300 psig. Note that production of $C_9$ analogs of the $C_8$ compounds respond similarly to increased pressure.

Addition of hydrogen to the reactor at atmospheric pressure was found to have no effect on the styrene-/ethyl benzene ratio in the product under the range of conditions studied. Excessive formation of coke leading to the reactor fouling was found to occur above 500° C.

The following examples show continuous thermal cracking of dehydration residue from the manufacture of styrene in a stirred tank reactor. The reactor was a 300 ml., 316 SS, autoclave modified for high temperature operation. Feed was preheated to 300° C. using a fluidized sand bath. The reactor was heated by an external sleeve-shaped furnace and its temperature was controlled by an Athena temperature controller. To prevent reactor fouling by coking at high temperature, power to the furnace was automatically cut off when the outside wall temperature reached 500° C. Except as noted in the examples, combined overhead and bottoms product were withdrawn from the reactor through a dip tube inserted through the top of the reactor. Reactor liquid volume was determined by draining the reactor at the end of the run. Residence times reported are based on the drained liquid volume and were calculated by dividing drained liquid volume by the volume flow rate of feed. Actual residence times during the course of any given run may differ from the reported value by as much as 20% because of fluctuations in the reactor liquid level.

EXAMPLE 2

Dehydration residue containing 5.1 wt. percent monomeric components was thermally cracked at varying pressures in the stirred tank reactor described above. Reactor temperature was maintained at 400° C. and the residence time was 40 minutes. The results shown in Table II were obtained over a 18 hour run and are expressed as grams/100 grams of dehydration residue. Note the effect of pressure on product composition: high pressures (100 or 200 psig v. 0 psig) increases ethylbenzene and decreases styrene monomer in the product. The styrene/ethylbenzene ratio of the product obtained at 0 psig is about 5 times that obtained at 100 psig. When compared to results obtained in the tubular reactor, it is seen that the stirred tank reactor produces a product remarkably rich in ethylbenzene, regardless of the pressure employed.

TABLE II

|  | Pressure (psig) | | |
| --- | --- | --- | --- |
|  | 0 | 100 | 200 |
| Total $C_8$'s | 23.9 | 25.6 | 24.1 |
| Ethylbenzene | 16.7 | 21.6 | 20.4 |
| Styrene | 4.8 | 1.4 | 1.0 |
| Acetophenone | 2.3 | 2.6 | 2.6 |
| Toluene | 6.9 | 9.3 | 9.9 |
| Total $C_9$'s | 4.7 | 5.1 | 4.9 |
| Styrene/Ethylbenzene | 0.29 | 0.06 | 0.05 |

EXAMPLE 3

In this Example, the dehydration residue employed in Example II was subjected to thermal cracking in the stirred tank reactor over a long on-stream time (91 hours). The results shown in Table III were obtained at 400° C., 200 psig, and 60 minutes residence time. No evidence of corrosion or piting of the 316 SS reactor was found. No reactor fouling or coking occured during the run.

TABLE III

| Total $C_8$'s | 27.4 |
| --- | --- |
| Ethylbenzene | 24.0 |
| Styrene | 0.7 |
| Acetophenone | 2.7 |
| Toluene | 11.1 |
| Total $C_9$'s | 5.7 |
| Styrene/Ethylbenzene | 0.03 |

EXAMPLE 4

The effect of residence time in the stirred tank reactor is exemplified in the runs described in Table IV. In these runs, a dehydration residue containing 7.0 wt. percent monomeric components was cracked in the stirred tank reactor at 400° C. and 100 psig. The results shown were obtained over an 18 hour run.

TABLE IV

|  | Residence Time (Minutes) | |
| --- | --- | --- |
|  | 40 | 70 |
| Total $C_8$'s | 28.5 | 29.1 |
| Ethylbenzene | 21.6 | 22.9 |
| Styrene | 2.2 | 1.4 |
| Acetophenone | 4.7 | 4.8 |
| Toluene | 9.6 | 10.5 |
| Total $C_9$'s | 6.4 | 6.3 |
| Styrene/Ethylbenzene | 0.10 | 0.06 |

EXAMPLE 5

Dehydration residue containing 6.3 wt. percent monomeric components was cracked in the stirred tank reactor at 425° C. and 100 psig. Results shown in Table V were obtained over an 18 hour run.

TABLE V

|  | Residence Time (Minutes) | | |
| --- | --- | --- | --- |
|  | 30 | 50 | 60 |
| Total $C_8$'s | 30.5 | 29.9 | 31.7 |
| Ethylbenzene | 24.5 | 24.1 | 26.5 |
| Styrene | 1.3 | 0.9 | 0.8 |
| Acetophenone | 4.4 | 4.7 | 4.3 |
| Toluene | 10.7 | 10.9 | 12.8 |
| Total $C_9$'s | 5.2 | 5.0 | 5.5 |
| Styrene/Ethylbenzene | 0.05 | 0.04 | 0.03 |

EXAMPLE 6

Dehydration residue containing 6.3 wt. percent monomeric components was cracked in the stirred tank reactor at 425° C., 100 psig, and a residence time of 50 minutes. Overhead and bottoms product were collected separately from the reactor. The overhead to bottoms weight ratio was 7:3. Compositions of the two product streams and the residue feed are shown in Table VI. The bottoms product is a tar-like material that solidifies at room temperature but flows easily above 150° C.

TABLE VI

|  | Feed (wt %) | Overheads, wt % | Bottoms, wt % |
| --- | --- | --- | --- |
| Ethylbenzene |  | 40 | 1.2 |
| Styrene | 1.7 | 2 | 0.08 |
| Acetophenone | 2.1 | 6.3 | 0.6 |

EXAMPLE 7

Dehydration residue containing 6.3 wt. percent monomeric components was cracked in the stirred tank reactor at 425° C., 200 psig, and a residence time of 60 minutes. Results shown in Table VII were obtained over an 18 hour run.

TABLE VII

| Total $C_8$'s | 30.2 |
| --- | --- |
| Ethylbenzene | 25.0 |
| Styrene | 0.6 |
| Acetophenone | 4.5 |
| Toluene | 12.8 |
| Total $C_9$'s | 5.5 |
| Styrene/Ethylbenzene | 0.02 |

What is claimed is:

1. A process for the recovery of aromatic hydrocarbons from dehydration residues obtained in the preparation of styrene from alpha-methylbenzyl alcohol which comprises thermally cracking the residues at a temperature within the range from about 325° C.–475° C. and a pressure within the range from about 75 to 300 psig, withdrawing the cracked effluent and recovering liquid aromatic hydrocarbons.

2. The process of claim 1 wherein the dehydration residue is thermally cracked at a pressure within the range from about 100 to 250 psig.

3. The process of claim 2 wherein the dehydration residue is thermally cracked at a temperature within the range from about 350° C.–450° C.

4. The process of claim 2 wherein the dehydration residue is thermally cracked at a temperature within the range from about 400° C.–425° C.

5. The process of claim 1 or 3 wherein the dehydration residue is thermally cracked in a stirred tank reactor.

6. The processes of claim 5 wherein the ratio of reactor liquid volume/volumeric feed rate is within the range from about 40–70 minutes.

7. The process of claim 1 wherein the dehydration residue is a purge stream from the liquid phase dehydration of alpha-methylbenzyl alcohol.

* * * * *